United States Patent [19]

Inoue et al.

[11] Patent Number: 4,985,363
[45] Date of Patent: Jan. 15, 1991

[54] MICROORGANISM CAPABLE OF GROWING IN 50% OR MORE ORGANIC SOLVENT

[75] Inventors: Akira Inoue; Kouki Horikoshi, both of Tokyo, Japan

[73] Assignee: Research Development Corporation, Tokyo, Japan

[21] Appl. No.: 163,576

[22] Filed: Mar. 3, 1988

[30] Foreign Application Priority Data

Mar. 5, 1987 [JP] Japan .................................. 62-48662
Mar. 5, 1987 [JP] Japan .................................. 62-48663

[51] Int. Cl.$^5$ .......................... C12N 1/26; C12R 1/38; C12R 1/40
[52] U.S. Cl. ................................ 435/253.3; 435/247; 435/248; 435/281; 435/874; 435/877
[58] Field of Search ............. 435/243, 247, 248, 253.3

[56] References Cited

U.S. PATENT DOCUMENTS 4,259,444 3/1981 Chakrabarty ........................ 435/172
4,508,824 4/1985 Olsen ................................. 435/172.3

*Primary Examiner*—Richard A. Schwartz
*Assistant Examiner*—S. L. Nolan
*Attorney, Agent, or Firm*—Nixon & Vanderhye

[57] ABSTRACT

New microorganisms belonging to *Pseudomonas putida* or Pseudomonas sp., which are isolated from soil and have tolerance to one or more of hydrocarbons, alcohols, ethers, ketones and their derivatives or their mixture. These new microorganisms can be used in the fields of bioreactor, liquid-waste treatment, protein engineering, etc.

4 Claims, No Drawings

MICROORGANISM CAPABLE OF GROWING IN 50% OR MORE ORGANIC SOLVENT

BACKGROUND OF THE INVENTION

This invention relates to biologically pure cultures of microorganisms and, in particular, to biologically pure cultures of microorganisms tolerant to hydrocarbons, alcohols, ethers, ketones or mixtures thereof.

As conventional examples of culturing a microorganism in a medium containing hydrocarbons or their derivatives, there are such many reports as of the growing of Nocardia sp. in a medium containing hexane or hexadecane [R. L. Raymond, *Appl. Microbial.*, vol. 15, pp. 857~865 (1967)], the growing of Bacterium JOB5 in a medium contining cyclopentane or cyclohexane [J. Ooyama, J. W. Foster, *Antonie von Leenwenlook*, vol. 31, pp. 45~65 (1965)], the growing of *Pseudomonas* sp., Achromobacter sp., and *Nocardia* sp. in a medium containing benzene, ethyl benzene, toluene or xylene [D. Cleus and N. Walkes, *J, Gen. Microbial*, vol. 36, pp. 107~122 (1964)], etc. can be enumerated. However, these microorganisms are cultured by bringing the same into contact with hydrocarbons which are concentrated low or in the form of steam in any of the above cases because the hydrocarbons generally show toxicity to microorganisms. That is, when the fermentation is carried out by using these hydrocarbons as substrates, it is carried by supplying these compounds in the form of steam so that the compounds may not be brought into contact with microorganisms directly or by maintaining the compounds at low concentration (0.2% or less) at which a toxic effect is not shown. Consequently, in the fermentation using hydrocarbons as substrates, there are problems not only of low productivity but also of operation because of the difficulty in adjusting the substrates to low concentration. Furthermore, in case of using slightly water-insoluble substances, there is a disadvantage that the productivity becomes low in the microbial reaction owing to the low solubility of the substances.

SUMMARY OF THE INVENTION

In order to solve the foregoing problems, the present inventors have extensively searched soil to obtain a microorganism which can grow up in a medium containing a solvent such as hydrocarbon or the like in a high concentration, that is, a microorganism having a tolerance to a solvent such as hydrocarbon or the like. As a result, the present inventors found out microorganisms having the aforementioned tolerance and completed the present invention.

That is, the object of the present invention lies in providing new microorganisms belonging to *Pseudomonas putida* and *Pseudomonas* sp. and having tolerance to one or more of aliphatic hydrocarbons, alicyclic hydrocarbons, aromatic hydrocarbons, alcohols, ethers, ketones and their derivatives or their mixture.

Because microorganisms belonging to *Pseudomonas putida* and *Pseudomonas* sp. according to the present invention have excellent tolerance to a solvent containing hydrocarbons, alcohols, ethers, ketones and their derivatives or their mixtures which are commonly used, said microorganisms can be prevented from the saprophyte contamination by culturing the same in the presence of the above solvents In this case, because the heat killing is not required, it becomes possible to use thermolabile additives. In case of carrying out the culture by using these solvents as substrates, the substrates can be supplied at high concentrations. Thus, the improvement in productivity can be expected. In addition, in case that the substrate concentration is high as described above, the control over the addition of the substrate becomes easier. In case of toxic substances to be used for the culture by dissolving in these solvent, the concentration control also becomes possible. Similarly, in case of slightly water-soluble substances to be used also by dissolving in the solvents, they can be used at high concentrations. Thus, the present microorganisms can also contribute to the improvement in productivity in these respects.

Furthermore, the present strains are useful as supply sources of resistance genes, and by &he use of the present strains, the cell fusion of solvent tolerant microorganisms producing useful substances and the breeding of said microorganisms according to the gene engineering technology become possible. The present strains have such excellent effects as above, so that they can be utilized widely in the fields of bioreactor, liquid-waste treatment, protein engineering, etc.

DETAILED DESCRIPTION OF THE INVENTION

As specific examples of the present microorganisms, *Pseudomonas putida* STM-603, *Pseudomonas* sp. STM 801 and *Pseudomonas* sp. STM-904 can be enumerated. These strains can grow in a medium containing aliphatic hydrocarbons, alicyclic hydrocarbons, alcohols, ethers, ketones, aromatic hydrocarbons which are particularly highly toxic and their derivatives in a concentration as high as 0.3% or more. In addition, these strains can grow even in a medium containing the above compounds in a concentration as high as 50% or more. Thus, in the culture of these microorganisms, a substrate can be supplied in large quantities, whereby the improvement of productivity and the control over the substrate concentration become easier and the prevention of saprophyte contamination becomes possible. Furthermore, the improvement of productivity in the microbial reaction and the control over the concentration of toxic substances become possible by dissolving slightly water-soluble substances in various hydrocarbons. Still furthermore, these microorganisms enable the breeding of solvent-tolerant microorganisms producing useful substances by the application of the cell fusion and the gene recombination technology, and are also useful as supply sources of resistance genes.

These strains, i.e., STM-603, STM-801 and STM-904 were obtained by culturing soil which the present inventors collected from all over the country in media containing 0.% glucose, 0.25% yeast extract, 0.5% peptone and 50% solvent (aliphatic hydrocarbons, alicyclic hydrocarbons, aromatic hydrocarbons, alcohols, ethers and ketones) and then isolating colonies formed.

As specific examples of solvents, pentane, hexane, heptane, octane, isooctane, nonane, decane, 1- or 2-hexene, 1-octene, 1-dodecene, 1,3-pentadiene, 1,5-hexadiene, 1,7-octadiene, etc. as aliphatic hydrocarbons cyclopentane, cyclohexane, methyl cyclopentane, methyl cyclohexane, etc. as alicyclic hydrocarbons; toluene, xylene, styrene, ethyl benzene, chlorobenzene, etc. as aromatic hydrocarbons; 1-heptanol, 1-octanol, 1-decanol, etc. as alcohols; n-hexyl ether, n-butyl phenyl ether, diphenyl ehter, dibenzyl ether, methoxytoluene, etc. as ethers; and 2-pentanone, 2-hexanone, 2-heptanone, cyclohexanone, etc. as kentones can be enumerated.

Hereinafter, the bacteriological properties of the present strains, i.e., STM-603, STM-80and STM-904 and the identification results of the same will be given.

TABLE 1

| Solvent | Pseudomonas putida IFO 3738 | STM-603 |
|---|---|---|
| Toluene | − | + |
| P-xylene | − | + |
| Styrene | − | + |

(1) Bacteriological Properties of STM-603

A. Morphological Properties (24-hr Culture in a Bouillon Liquid Medium):
   a. Shape and size of the cell:
       Rod, 0.7~1.0 × 2~4μ
   b. Polymorphism of the cell: −
   c. Motility: +
   d. Sporulation: −
   e. Gram's stain: Negative B. State of Growth in Various Media (24-hr culture at 30° C.):
   a. Bouillon agar plate culture:
       Circular colonies of 0.5 to 1 mm with lustrously flesh-colored surface.
   b. Bouillon agar slant culture:
       Grown on the surface of the medium.
   c. Bouillon liquid culture:
       Grown
   d. Bouillon gelatin stab culture:
       No gelatin liquefaction takes place.

C. Physiological Properties
   a. Nitrate reduction: Negative
   b. Starch hydrolysis: Negative
   c. Poly-β-hydroxybutyrate hydrolysis: Negative
   d. Tween 80 hydrolysis: Negative
   e. Arginine hydrolysis: Positive
   f. Pigment formation (King B medium):
       Yellowish green, water-soluble fluorochrome is formed.
   g. Oxydase: Positive
   h. Catalase: Positive
   i. Growth range:
       pH: 5.0~9.5
       Temperature: Not grown at 41° C.
   j. Behavior toward oxygen: Aerobic
   k. O-F test: Oxidative
   l. Citrate utilization: Positive
   m. Levan production from sucrose: Negative
   n. DNase production: Negative
   o. Acylamidase production: Negative
   p. Assimilation:
       D-glucose +
       D-fructose +
       D-xylose +
       D-maltose −
       Sucrose −
       Lactose −
       D-trehalose −
       Mannitol −
       2-ketogluconic acid +
       L-valine +
       β-alanine +
       DL-arginine +
       Acetoamido −
       Meso-inositol −
       Benzylamine +
       Geraniol −

On the basis of the above bacteriological properties, the screening was carried out according to *Bergey's Manual of Determinative Bacteriology* (8th ed., 1975). As a result, these properties were compatible with those of *Pseudomonas putida*. However, *Pseudomonas putida* is intolerant to hydrocarbons. The tolerance of a standard strain of *Pseudomonas putida* and the present strain STM-603 to various solvents were examined. The results were given in Table 1.

From the facts that the strain STM-603 and *Pseudomonas putida* had morphological, physiological and bacteriological properties in common but differed from one another in the behavior toward the solvent tolerance as described above, the present strain was recognized as a new strain belonging to *Pseudomonas putida* and designated as *Pseudomonas putida* var. STM-603. The present strain has been deposited in Fermentation Research Institute of Agency of Industrial Science and Technology with the accession number FERM BP-1751 (Bikoken-kinki No. 9228).

(2) Bacteriological Properties of STM-801

A. Morphological Properties (24-hr Culture in a Bouillon Liquid Medium)
   a. Shape and size of the cell:
      Rod, 0.7~1.0 × 2~15μ
   b. Polymorphism of the cell: —
   c. Motility: + or —
   d. Sporulation: —
   e. Gram's stain: Negative B. State of Growth in Various Media (24-hr culture at 30° C.):
   a. Bouillon agar plate culture:
      Circular colonies of 0.5 to 1 mm with lustrously flesh-colored surface.
   b. Bouillon agar slant culture:
      Grown on the surface of the medium.
   c. Bouillon liquid culture:
      Grown
   d. Bouillon gelatin stab culture:
      No gelatin liquefaction takes place.

C. Physiological Properties:
   a. Nitrate reduction: Negative
   b. Starch hydrolysis: Negative
   c. Poly-β-hydroxybutyrate hydrolysis: Negative
   d. Tween 80 hydrolysis: Negative
   e. Arginine hydrolysis: Positive
   f. Pigment formation (King B medium):
      Yellowish green, water-soluble fluorochrome is formed.
   g. Oxydase: Positive
   h. Catalase: Positive
   i. Growth range:
      pH: 5.0~9.0
      Temperature: Not grown at 41° C.
   j. Behavior toward oxygen: Aerobic
   k. O-F test: Oxidative
   l. Citrate utilization: Positive
   m. Levan production from sucrose: Negative
   n. DNase production: Negative
   o. Acylamidase production: Negative
   p. Assimilation:
      D-glucose +
      D-fructose +
      D-xylose +
      D-maltose —
      Sucrose —
      Lactose —
      D-trehalose —
      Mannitol —
      2-ketogluconic acid +
      L-valine +
      β-alanine +
      DL-arginine +
      Acetoamido —
      Meso-inositol —
      Benzylamine +
      Geraniol —

(3) Bacteriological properties of STM-904

A. Morphological Properties (24-hr. Culture in a Bouillon Liquid Medium):
   a. Shape and size of the cell:
      Rod, 0.7~1.0 × 3~15μ
   b. Polymorphism of the cell: —
   c. Motility: + or —
   d. Sporulation: —
   e. Gram's stain: Negative B. State of Growth in Various Media (24-hr. culture at 30):
   a. Bouillon agar plate culture:
      Circular colonies of 0.5 to 1 mm with lustrously flesh-colored surface.
   b. Bouillon agar slant culture:
      Grown on the surface of the -continued

|   |   |   |
|---|---|---|
|   | medium. |   |
| c. | Bouillon liquid culture: |   |
|   | Grown |   |
| d. | Bouillon gelatin stab culture: |   |
|   | No gelatin liquefaction takes place. |   |
| C. | Physiological Properties: |   |
| a. | Nitrate reduction: | Negative |
| b. | Starch hydrolysis: | Negative |
| c. | Poly-β-hydroxybutyrate hydrolysis: | Negative |
| d. | Tween 80 hydrolysis: | Negative |
| e. | Arginine hydrolysis: | Positive |
| f. | Pigment formation (King B medium): |   |
|   | Not formed. |   |
| g. | Oxydase: | Positive |
| h. | Catalase: | Positive |
| i. | Growth range: |   |
|   | pH:  5.0~9.0 |   |
|   | Temperature: Not grown at 41° C. |   |
| j. | Behavior toward oxygen: | Aerobic |
| k. | O-F test: | Oxidative |
| l. | Citrate utilization: | Positive |
| m. | Levan production from sucrose: | Negative |
| n. | DNase production: | Negative |
| o. | Acylamidase production: | Negative |
| p. | Assimilation: |   |
|   | D-glucose | + |
|   | D-fructose | + |
|   | D-xylose | + |
|   | D-maltose | − |
|   | Sucrose | − |
|   | Lactose | − |
|   | D-trehalose | − |
|   | Mannitol | − |
|   | 2-ketogluconic acid | + |
|   | L-valine | + |
|   | β-alanine | + |
|   | DL-arginine | + |
|   | Acetoamido | − |
|   | Meso-inositol | − |
|   | Benzylamine | + |
|   | Geraniol | − |

On the basis of bacteriological properties as given in above (2) and (3), the screening was carried out according to Bergey's Manual of Determinative Bacteriology (8th ed., 1975). As a result, these strains STM-801 and STM-904 were found to be similar to Pseudomonas putida as a known strain. Thus, the present inventors have made a further detailed comparison between the present strains STM-801 and STM-904 and a standard strain of Pseudomonas putida IFO 3738 with respect to their bacteriological properties, thereby obtaining the following results (see Table 2 also):

(I) The cell size of Pseudomonas putida is 0.7 to 1.0μ by 2 to 4μ, while that of STM-801 and STM-904 are respectively 0.7 to 1.0μ by 2 to 15μ and 0.7 to 1.0μ by 2 to 15μ. That is, the size of the prestrains is 3 to 4 times that of Pseudomonas putida.

(2) In case of Pseudomonas putida, all the cells show the motility. However, in case of STM-801 and STM-904, some show the motility but the other do not.

(3) In case of Pseudomonas putida, yellowish green water-soluble fluorochrome is formed. In case of STM 801 and STM-904, the former forms the same pigment as above but the latter does not.

(4) Regarding the solvent tolerance with respect to toluene, p-xylene and styrene, Pseudomonas putida does not show a tolerance at all while STM-801 and STM-904 show tolerance.

From these results, it is recognized that the strains STM-801 and STM-904 correspond to new species because they are obviously different from Pseudomonas putida and because there is no known species corresponding to these strains. So, the present inventors designated the strains STM-801 and STM-904 as Pseudomonas sp. STM-801 and Pseudomonas sp. STM-904 respectively.

TABLE 2

|   |   | Pseudomonas putida IFO 3738 | STM-801 | STM-904 |
|---|---|---|---|---|
| (1) | Size of Cell | 0.7~1.0 × 2~4μ | 0.7~1.0 × 2~15μ | 0.7~1.0 × 3~15μ |
| (2) | Motility | + | + or − | + or − |
| (3) | Pigment Formation | Yellowish green, water-soluble fluorochrome | Yellowish green, water-soluble fluorochrome | Not formed |
| (4) | Solvent Tolerance: |   |   |   |
|   | Toluene | − | + | + |
|   | P-xylene | − | + | + |

TABLE 2-continued

| | Pseudomonas putida IFO 3738 | STM-801 | STM-904 |
|---|---|---|---|
| Styrene | − | + | + |

Said *Pseudomonas* sp. STM-801 and *Pseudomonas* sp. STM-904 were deposited in Fermentation Research Institute of Agency of Industrial Science and Technology respectively with the accession numbers FERM BP-1749 (Bikoken-kinki No. 9226) and FERM BP 1750 (Bikoken kinki No. 9227).

As a medium for culturing these strains, an ordinary medium containing a carbon source, a nitrogen source, an inorganic ion, etc. is used.

As a carbon source, any of those which can be assimilated, for example, sugars such as glucose, fructose, xylose, starch hydrolysate, etc., hydrocarbons such as toluene. p-xylene, etc., alcohols such as methanol, ethanol, etc., etc. can be used. As a nitrogen source, yeast extract, dry yeast, peptone, meat extract, corn steep liquor, casamino acid, ammonium chloride, ammonium sulfate, urea, sodium nitrate, etc. are used. As an inorganic ion, phosphoric acid ion, magnesium ion, iron ion, calcium ion, potassium ion, copper ion, manganese ion, etc. are used.

The culture was carried out at pH 5 to 9 at 20° to 40° C. under aerobic conditions.

TEST EXAMPLE 1

*Pseudomonas putida* var. STM-603, *Pseudomonas* sp. STM-801, *Pseudomonas* sp. STM-904 and various known strains were respectively inoculated into the prescribed media (pH 7.0) of respective strains. Then, each 5ml of various solvents given in Table 3 was added to each 5ml of said media. After culturing the resulting media at 37° C. for 48 hours, the growth of each strain was compared. The results were given in Table 3.

TABLE 3

Comparison of Solvent Tolerance of Various Strains

| | Cyclohexane | Toluene | P-xylene | Styrene |
|---|---|---|---|---|
| *Pseudomonas putida* var. STM-603 | + | + | + | + |
| Pseudomonas sp. STM-801 | + | + | + | + |
| Pseudomonas sp. STM-904 | + | + | + | + |
| *Pseudomonas aruginosa* IFO-3924 | − | − | − | − |
| *Pseudomonas fluorescens* IFO-3507 | − | − | − | − |
| *Pseudomonas putida* IFO-3738 | + | − | − | − |
| *Pseudomonas pseudoalcaligenes* ATCC-12815 | − | − | − | − |
| *Arthrobacter globiformus* IFO-3062 | − | − | − | − |
| *Agrobacterium tumefaciens* IFO-3058 | − | − | − | − |
| *Escherichia coli* IFO-3806 | − | − | − | − |
| *Bacillus cereus* IFO-3131 | − | − | − | − |
| *Bacillus coagulans* IFO-3557 | − | − | − | − |

−: Not grown +: Grown (O.D$_{660}$>0.50)
Bouillon liquid medium: Pseudomonas, Arthrobacter, Agrobacterium and Bacillus
LB medium: Escherichia

EXAMPLE 1

A medium prepared by adding 1.0l of distilled water to 1.0 of glucose, 2.5g of yeast extract and 5.0g of peptone and adjusted to pH 7.0 was dispensed in 100ml portions into 500ml ribbed conical flasks, in which *Pseudomonas putida* var. STM-603 was inoculated without sterilizing said flasks. After adding each 30ml of toluene to the flasks, the culture as carried out at 37° C. for 48 hours. As a result, 1.2mg/ml of *Pseudomonas putida* var. STM-603 cell mass was obtained, where the contamination and the growth of other microorganisms were not observed.

EXAMPLE 2

The same medium as &hat of Example 1 was prepared, dispensed in 5ml portions into large test tubes and steamsterilized at 121° C. for 15 minutes. Then, *Pseudomonas putida* var. STM-603 was inoculated in the large test tubes, to which each 5ml of various solvents given in Table 4 was added. The culture was carried out at 37° C. using a test tube shaker. The state of growth after 48 hours was given in Table 4. The growth was monitored by measuring turbidity (wave length: 660nm, a colorimeter "Spectronic 21" manufactured by Bausch & Lomb Corp.).

TABLE 4

Tolerance of *Pseudomonas putida* var. STM-603 to Various Solvents

| Solvent | State of Growth |
|---|---|
| Aliphatic hydrocarbons: | |
| n-pentane | + |
| n-hexane | + |
| n-heptane | + |
| n-octane | + |
| isooctane | + |
| n-nonane | + |
| n-decane | + |
| 1- or 2-hexene | + |
| 1-octene | + |
| 1-dodecene | + |
| 1,3-pentadiene | ± |
| 1,5-hexadiene | + |
| 1,7-octadiene | + |
| Alicyclic hydrocarbons: | |
| cyclopentane | + |
| methyl cyclopentane | + |
| cyclohexane | + |
| methyl cyclohexane | + |

TABLE 4-continued

Tolerance of *Pseudomonas putida* var. STM-603 to Various Solvents

| Solvent | State of Growth |
|---|---|
| butyl cyclohexane | + |
| cyclooctane | + |
| Aromatic hydrocarbons: | |
| toluene | + |
| p-xylene | + |
| o-,m-p-xylene | + |
| chlorobenzene | + |
| o-dichlorobenzene | + |
| 1,2,4-trichlorobenzene | + |
| bromobenzene | + |
| ethyl benzene | + |
| propyl benzene | + |
| styrene | + |
| Alcohols: | |
| 1-heptanol | + |
| 1-octanol | + |
| 1-decanol | + |
| Ethers: | |
| n-hexyl ether | + |
| n-butyl phenyl ether | + |
| diphenyl ether | + |
| dibenzyl ether | + |
| methoxytoluene | + |

±: Grown ($0 < O.D_{660} < 0.50$)
+: Grown ($O.D_{660} > 0.50$)

EXAMPLE 3

The same medium as that of Example 1 Was prepared, dispensed in 5m L portions into large test tubes and steamsterilized a& 121° for 15 minutes. Then, *Pseudomonas putida* var. STM-603 was inoculated in the test tubes, to which each 0.25ml of various solvents given in Table 5 was added. The culture was carried out at 37° C. using a test tube shaker. The state of growth after 48 hours was given in Table 5. The growth was monitored by measuring turbidity (wave length: 660nm, a colorimeter "Spectronic 21" manufactured by Bausch & Lomb Corp.).

TABLE 5

| Solvent | Strain STM-603 |
|---|---|
| Ketones: | |
| 2-pentanone | ± |
| 2-hexanone | ± |
| 2-heptanone | + |
| cyclohexane | ± |

—: Not grown
±: Grown ($0 < O.D_{660} < 0.50$)
+: Grown ($O.D_{660} > 0.50$)

EXAMPLE 4

A medium prepared by adding 1.0l of distilled water to b 1.0g of glucose, 2.5g of yeast extract and 5.0g of peptone and adjusted to pH 7.2 was dispensed in 100ml portions into 500 ml ribbed flasks, in which *Pseudomonas* sp. STM-801 was inoculated without sterilizing said flasks. After adding each 30ml of toluene to the flasks, the culture was carried out at 37° C. for 48 hours. As a result, 1.1mg/ml of *Pseudomonas* sp. STM-801 cell mass was obtained, there the contamination and the growth of other microorganisms were not observed.

EXAMPLE 5

The same medium as that of Example 1 was prepared, dispensed in 5ml portions into large test tubes and steamsterilized at 121° C. minutes. Then, *Pseudomonas* sp. STM-801 and *Pseudomonas* sp. STM-904 were respectively inoculated in the large test tubes, to which each 5ml of various solvents given in Table 6 was added. The culture was carried out at 37° C. using a test tube shaker. The state of growth after 48 hours was given in Table 6. The growth was monitored by measuring turbidity (wave length: 660nm, a colorimeter "Spectronic 21" manufactured by Bausch & Lomb Corp.).

TABLE 6

Tolerance of *Pseudomonas* sp. STM-801 and *Pseudomonas* sp. STM-904 to Various Solvent

| | State of Growth | |
|---|---|---|
| Solvent | STM-801 | STM-904 |
| Aliphatic hydrocarbons: | | |
| n-pentane | + | + |
| n-hexane | + | + |
| n-heptane | + | + |
| n-octane | + | + |
| isooctane | + | + |
| n-nonane | + | + |
| n-decane | + | + |
| 1- or 2-hexene | + | + |
| 1-octene | + | + |
| 1-dodecene | + | + |
| 1,3-pentadiene | ± | ± |
| 1,5-hexadiene | + | + |
| 1,7-octadiene | + | + |
| Alicyclic hydrocarbons: | | |
| cyclopentane | + | + |
| methyl cyclopentane | + | + |
| cyclohexane | + | + |
| methyl cyclohexane | + | + |
| butyl cyclohexane | + | + |
| cyclooctane | + | + |
| Aromatic hydrocarbons: | | |
| toluene | + | + |
| p-xylene | + | + |
| o-,m-p-xylene | + | + |
| chlorobenzene | + | + |
| o-dichlorobenzene | + | + |
| 1,2,4-trichlorobenzene | + | + |
| bromobenzene | + | + |
| ethyl benzene | + | + |
| propyl benzene | + | + |
| styrene | + | + |
| Alcohols: | | |
| 1-heptanol | + | + |
| 1-octanol | + | + |
| 1-decanol | + | + |
| Ethers: | | |
| n-hexyl ether | + | + |
| n-butyl phenyl ether | + | + |
| diphenyl ether | + | + |
| dibenzyl ether | + | + |
| methoxytoluene | + | + |

±: Grown ($0 < O.D_{660} < 0.50$)
+: Grown ($O.D_{660} > 0.50$)

EXAMPLE 6

The same medium as that of Example 1 was prepared, dispensed in 5ml portions into large test tubes and steamsterilized at 121° C. for 15 minutes. Then, *Pseudomonas* sp. STM-801 and *Pseudomonas* sp. STM 904 were respectively inoculated in the test tubes, to each of which each 0.25ml of various solvents given in Table 7 was added. The culture was carried out at 37° C. using a test tube shaker. The state of growth after 48 hours was given in Table 7. The growth was monitored by measuring turbidity (wave length: 660nm, a colorimeter "Spectronic 21" manufactured by Bausch & Lomb Corp.).

TABLE 7

| Solvent | State of Growth | |
| --- | --- | --- |
| | STM-801 | STM-904 |
| Ketones: | | |
| 2-pentanone | ± | ± |
| 2-hexanone | ± | ± |
| 2-heptanone | + | + |
| cyclohexane | ± | ± |

−: Not grown
±: Grown ($0 < O.D_{660} < 0.50$)
+: Grown ($O.D_{660} > 0.50$)

What is claimed is:

1. A biologically pure culture of a microorganism which is characterized by being capable of growing in the presence of 50 v/v % or more of an organic solvent selected from the group consisting of aliphatic hydrocarbons, alicyclic hydrocarbons, aromatic hydrocarbons, alcohols, ethers and ketones, said microorganism being selected from the group consisting of *Pseudomonas putida* var. STM-603 (FERM BP-1751), *Pseudomonas* sp. STM-801 (FERM BP-1749) and *Pseudomonas* sp. STM-904 (FERM BP-1750).

2. A biologically pure culture of a microorganism as claimed in claim 1, wherein the microorganism is *Pseudomonas putida* var. STM-603 (FERM BP-1751).

3. A biologically pure culture of a microorganism as claimed in claim 1, wherein the microorganism is *Pseudomonas* sp. STM-801 (FERM BP-1749).

4. A biological pure culture of a microorganism is *Pseudomonas sp.* STM-904 (FERM BP-1750).

* * * * *